(12) United States Patent
Fang et al.

(10) Patent No.: US 8,877,959 B2
(45) Date of Patent: Nov. 4, 2014

(54) METHOD FOR PREPARING PYRUVATE ESTER

(75) Inventors: Shun-I Fang, Taipei (TW); Cheng-Fa Hsieh, Taipei (TW); Chien-Chuan Shih, Taipei (TW)

(73) Assignee: China Petrochemical Development Corporation Taipei (Taiwan), Taipei (TW)

( * ) Notice: Subject to any disclaimer, the term of this patent is extended or adjusted under 35 U.S.C. 154(b) by 0 days.

(21) Appl. No.: 13/619,626

(22) Filed: Sep. 14, 2012

(65) Prior Publication Data
US 2014/0031581 A1    Jan. 30, 2014

(30) Foreign Application Priority Data

Jul. 30, 2012 (TW) .............................. 101127415 A

(51) Int. Cl.
*C07C 69/716* (2006.01)
(52) U.S. Cl.
USPC ........................................................ 560/174
(58) Field of Classification Search
CPC .................................................. C07C 67/313
See application file for complete search history.

(56) References Cited

U.S. PATENT DOCUMENTS 4,480,135 A * 10/1984 Esposito et al. .............. 568/385
5,053,527 A   10/1991 Christidis et al.

FOREIGN PATENT DOCUMENTS

CN    101318903 A      12/2008
JP    05-017404 a   *  1/1993

OTHER PUBLICATIONS

Serrano et al, Chemical Communications, Turning TS-1 Zeolite into a Highly Active Catalyst for Olefin Epoxidation with Organic Hydroperoxides, 2009, pp. 1407-1409.*

* cited by examiner

*Primary Examiner* — Paul A Zucker
(74) *Attorney, Agent, or Firm* — Edwards Wildman Palmer LLP; Peter F. Corless; Richard B. Emmons

(57) ABSTRACT

A method for preparing a pyruvate ester is disclosed. In the method of the present invention, a lactate ester is oxidized by hydrogen peroxide in the presence of a Ti—Si molecular sieve catalyst. In the present invention, the Ti—Si molecular sieve catalyst is easily filtered and recycled, the reaction conditions are mild due to the usage of hydrogen peroxide, the process is simple and easily performed, the conversion rate of the lactate ester is high, and the selectivity of the pyruvate ester is high.

8 Claims, No Drawings

METHOD FOR PREPARING PYRUVATE ESTER

CROSS-REFERENCES TO RELATED APPLICATIONS

This application claims under 35 U.S.C. §119(a) the benefit of Taiwanese Application No. 101127415, filed Jul. 30, 2012, the entire contents of which is incorporated herein by reference.

FIELD OF INVENTION

The present invention relates to methods for preparing pyruvate esters, and more particularly, to a method for preparing a pyruvate ester in a solid-liquid reaction system having a Ti—Si molecular sieve and an oxidant.

Background of the Invention

Pyruvate esters are critical intermediates in organic syntheses, and are widely used in the medical, agrochemical, cosmetics and laser fields. Currently, there are two main methods for preparing pyruvate esters in industry. Tartaric acid is dehydrated and then esterified. However, the dehydration is performed at a high temperature, such that a slag is easily formed in a reactor, and the yield of the reaction is low due to the dehydration of pyruvate esters at the high temperature. Thus, there is a need to prepare pyruvate esters under mild conditions.

There are many methods and materials for preparing pyruvate esters, wherein the simplest reaction is performed by using lactic acid esters as materials in a gas phase or a liquid phase. In the gas phase reaction, a catalyst is a composite of aluminum oxide, a metal catalyst (such as Pt, Ag or V) and air or oxygen, and the reaction is performed at 190 to 500° C. to form pyruvate esters. The cost of the gas phase reaction is high due to the huge energy consumption.

There are various liquid phase reactions such as the $NO_2$ oxidation or $KMnO_4$ oxidation. CN101318903A discloses that a lactate ester is oxidized via a halo-organic oxidizing agent in acetone under the catalysis of a nitrogen oxide and an alkali so as to form a pyruvate ester. In this method, $NO_2$ produced in the reaction can be recycled if there is a resource of $NO_x$. U.S. Pat. No. 5,053,527 discloses that a lactate ester is oxidized to a pyruvate ester via $MnO_4$ or $MnO_4$ and $CuSO_4$. However, $MnO_4$ has strong capability of oxidation, there are many byproducts of the reaction, the product is not easily purified, the yield is poor, and MnO4 causes pollutions.

In addition, when the lactate ester is directly oxidized to form the pyruvate ester, the C—C bond of the lactate ester is easily broken to form an aldehyde and carbon dioxide, and thus to adversely affect the yield of the pyruvate ester and the subsequent purification. Hence, there is a need to develop a suitable oxidant, a catalyst system, and proper reaction conditions.

SUMMARY OF THE INVENTION

The present invention provides a method for preparing a pyruvate ester, comprising the step of performing an oxidation of a lactate ester by hydrogen peroxide in the presence of a Ti—Si molecular sieve to obtain a pyruvate ester having a structure of formula (I):

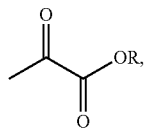

wherein R is a linear or branched $C_{1-4}$ alkyl.

In accordance with the present invention, the lactate ester has a structure of formula (II):

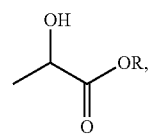

wherein R is a linear or branched $C_{1-4}$ alkyl, and the alkyl group is the same as the alkyl group of the pyruvate ester to be prepared.

In accordance with the present invention, the Ti—Si molecular sieve may have, but is not limited to, a structure of MFI, MEL, BEA, ZSM-48, MTW, MCM-41 or MWW. Preferably, the Ti—Si molecular sieve of the present invention has the MFI structure. Preferably, a mole ratio of Ti to Si in the molecular sieve is in a range from 0.0167:1 to 0.1:1.

In the method for preparing a pyruvate ester of the present invention, the lactate ester can be optionally oxidized in a solvent. The solvent may be an alcohol or an aromatic hydrocarbon, wherein the alcohol may be ethanol, n-propanol, isopropanol, n-butanol, isobutanol or t-butanol, and the aromatic hydrocarbon may be benzene, toluene, xylene, trimethylbenzene or ethylbenzene.

In accordance with the present invention, a weight ratio of the solvent to the lactate ester is preferably in a range from 10:1 to 0:1.

In accordance with the present invention, a mole ratio of the hydrogen peroxide to the lactate ester is preferably in a range from 1:1 to 3:1, and more preferably in a range from 1:1 to 1.25:1.

In accordance with the present invention, the lactate ester is oxidized at a temperature, which is preferably in a range from 40 to 110° C., and more preferably in a range from 50 to 80° C.

In the method of the present invention, the Ti—Si molecular sieve is the solid catalyst, which is easily recycled via filtration, and the reaction conditions are mild due to the reaction system with hydrogen peroxide. The method of the present invention is easily operated, eliminates the energy consumption of the gas phase reaction in the prior art, and has a high conversion rate of the lactate ester and a high selectivity of the pyruvate ester.

DETAILED DESCRIPTION OF THE PREFERRED EMBODIMENTS

Preparation 1

Preparation of Ti—Si Molecular Sieve

The Ti—Si molecular sieves in the present invention were prepared by this method.

1.98 g of tetra-n-butyl titanate was provided in a 500 ml flask with a vacuum system and a constant pressure feed system, and was sealed under nitrogen. The sealed flask was cooled down to 5° C. 30 g of tetraethyl silicate was dropped into the sealed flask via the constant pressure feed system, and then stirred at 5° C. for 1 hour. 56 g of tetra-n-propylammonium hydroxide in isopropanol (20 wt %) was dropped into the sealed flask via the constant pressure feed system, and then stirred at 5° C. for 1 hour. Subsequently, 44.8 g of water was dropped into the sealed flask via the constant pressure feed system, and then stirred at 5° C. for 1 hour. The mixture was warmed up to the room temperature, and then stirred for 1 hour. The mixture was heated to 85° C., and placed at 85° C. for 2 hours to remove isopropanol in the flask. Thus, the Ti—Si template synthetic gel was formed. Then, 10.8 g of Ludox AS-40 colloidal silica (Sigma-Aldrich) was dispersed in 73.5 g of water to form a colloidal silica dispersion solution. After the residual alcohol was removed, the Ti—Si template synthetic gel and the colloidal silica dispersion solution were mixed and stirred for 1 hour, so as to form a Ti—Si template synthetic gel mixture. The Ti—Si template synthetic gel mixture was provided and sealed in a stainless can with a Teflon lining, and heated in a water bath at 180° C. for 120 hours (surface pressure: 22 kg/cm$^2$). The solid product was separated from the liquid, and washed with pure water to be neutral. The solid was dried at 100° C., and calcinated for 8 hours, so as to form a catalyst sample. The average particle size was 14.13 μm, and the median diameter ($d_{50}$) of the Ti—Si molecular sieve with the MFI structure was 11.77.

Embodiments 1 and 2

Embodiments 1 and 2 were performed to select a solvent for reactions. Referring to the components listed in Table 1, 1 g of the Ti—Si molecular sieve of Preparation 1, 20 g of the solvent shown in Table 1 and 5 g of ethyl lactate were provided in a 250 ml flask with a condenser tube and a stirring system. After the mixture was heated to 70° C., 4.11 g of hydrogen peroxide solution (35 wt %) was dropped into the reaction, and the preparation of ethyl pyruvate was performed. The introduction of hydrogen peroxide was performed for 1 hour, and then the reaction was performed at 70° C. for 5 hours. Upon stopping the reaction, the Ti—Si molecular sieve catalyst was separated from the reaction solution. The solution was analyzed by gas chromatography (Varian CP-3800, VF-1 column) and titration (Mettler Toledo DL 50). The results were shown in Table 1.

TABLE 1

| Embodiment | Solvent | $X_{EL}$ (%) | $S_{EP}$ (%) | $X_{H2O2}$ (%) | $S_{H2O2}$ (%) | $Y_{EP}$ (%) |
|---|---|---|---|---|---|---|
| 1 | tert-butanol | 83.37 | 95.2 | 100 | 81.2 | 79.37 |
| 2 | toluene | 68.26 | 90.31 | 99.83 | 60.45 | 61.65 |

$X_{EL}$: conversion rate of ethyl lactate = consumption moles of ethyl lactate/initial total moles of ethyl lactate × 100%
$S_{EP}$: selectivity of ethyl pyruvate = produced moles of ethyl pyruvate/consumption moles of ethyl lactate × 100%
$X_{H2O2}$: conversion rate of hydrogen peroxide = consumption moles of hydrogen peroxide/initial total moles of hydrogen peroxide × 100%
$S_{H2O2}$: selectivity of hydrogen peroxide = produced moles of ethyl pyruvate/consumption moles of hydrogen peroxide × 100%
$Y_{EP}$: yield of ethyl pyruvate = conversion rate of ethyl lactate × selectivity of ethyl pyruvate × 100%

Comparative Examples 1 to 4

Comparative Examples 1 to 4 were performed as Embodiment 2 except the solvents shown in Table 2. The results were shown in Table 2.

TABLE 2

| Comparative Example | solvent | $X_{EL}$ (%) | $S_{EP}$ (%) | $X_{H2O2}$ (%) | $S_{H2O2}$ (%) | $Y_{EP}$ (%) |
|---|---|---|---|---|---|---|
| 1 | — | 20.19 | 84.27 | 95.17 | 82.72 | 17.01 |
| 2 | water | 84.06 | 40.86 | 100 | 33.4 | 34.35 |
| 3 | ethyl acetate | 34.85 | 27.12 | 81.9 | 11.52 | 9.45 |
| 4 | acetonitrile | 22.24 | 92.75 | 54.63 | 35.01 | 20.63 |

In Comparative Example 1, only ethyl lactate was used without any solvents.

Embodiments 3 to 7

Embodiments 3 to 7 were performed to adjust the temperature of reactions. Referring to the components listed in Table 3, 1 g of the Ti—Si molecular sieve of Preparation 1, 20 g of tert-butanol and 5 g of ethyl lactate were provided in a 250 ml flask with a condenser tube and a stirring system. The reaction was heated to the temperature shown in Table 3. Then, 4.11 g of hydrogen peroxide solution (35 wt %) was dropped into the reaction, and the preparation of ethyl pyruvate was performed. The introduction of hydrogen peroxide was performed for 1 hour, and then the reaction was performed at the temperature shown in Table 3 for 5 hours. Upon stopping the reaction, the Ti—Si molecular sieve catalyst was separated from the reaction solution. The solution was analyzed by gas chromatography and titration. The results were shown in Table 3.

TABLE 3

| Embodiment | Temperature (° C.) | $X_{EL}$(%) | $S_{EP}$(%) | $X_{H2O2}$(%) | $S_{H2O2}$(%) |
|---|---|---|---|---|---|
| 3 | 50 | 76.68 | 73.94 | 88.59 | 63.86 |
| 4 | 65 | 70.38 | 80.59 | 94.71 | 59.9 |
| 5 | 70 | 83.37 | 95.45 | 100 | 79.52 |
| 6 | 75 | 83.34 | 96.66 | 100 | 80.64 |
| 7 | 80 | 84.54 | 94.10 | 99.42 | 79.77 |

Embodiments 8 to 11

Embodiments 8 to 11 were performed to adjust the ratio of ethyl lactate to hydrogen peroxide. Referring to the components listed in Table 4, 1 g of the Ti—Si molecular sieve of Preparation 1, 20 g of tert-butanol and 5 g of ethyl lactate were provided in a 250 ml flask with a condenser tube and a stiffing system. The reaction was heated to 75° C. Then, the amount of hydrogen peroxide solution (35 wt %) shown in Table 4 was dropped into the reaction, and the preparation of ethyl pyruvate was performed. The introduction of hydrogen peroxide was performed for 1 hour, and then the reaction was performed for 5 hours. Upon stopping the reaction, the Ti—Si molecular sieve catalyst was separated from the reaction solution. The solution was analyzed by gas chromatography and titration. The results were shown in Table 4.

TABLE 4

| Embodiment | EL:$H_2O_2$(mole ratio) | $x_{EL}$(%) | $S_{EP}$(%) | $X_{H2O2}$(%) | $S_{H2O2}$(%) |
|---|---|---|---|---|---|
| 8 | 1:1 | 83.34 | 96.66 | 100 | 80.64 |
| 9 | 1:1.25 | 93.18 | 87.75 | 100 | 70.28 |
| 10 | 1:1.5 | 94.13 | 75.25 | 100 | 46.87 |
| 11 | 1:3 | 90.55 | 47.77 | 94.4 | 15.33 |

Comparative Example 5

Comparative Example 5 was performed as Embodiments 8 to 11 except the mole ratio shown in Table 5. The results were shown in Table 5.

TABLE 5

| Comparative Example | EL:H₂O₂ (mole ratio) | $X_{EL}$(%) | $S_{EP}$(%) | $X_{H2O2}$(%) | $S_{H2O2}$(%) |
|---|---|---|---|---|---|
| 5 | 1:0.1 | 5.55 | 20.39 | 99.88 | 0.47 |

Embodiments 12 to 17

Embodiments 12 to 17 were performed to adjust the ratio of the solvent to ethyl lactate. Referring to the components listed in Table 6, 1 g of the Ti—Si molecular sieve of Preparation 1, the amount of tert-butanol shown in Table 6 and 5 g of ethyl lactate were provided in a 250 ml flask with a condenser tube and a stiffing system. The reaction was heated to 70° C. Then, 4.11 g of hydrogen peroxide solution (35 wt %) was dropped into the reaction, and the preparation of ethyl pyruvate was performed. The introduction of hydrogen peroxide was performed for 1 hour, and then the reaction was performed for 5 hours. Upon stopping the reaction, the Ti—Si molecular sieve catalyst was separated from the reaction solution. The solution was analyzed by gas chromatography and titration. The results were shown in Table 6.

TABLE 6

| Embodiment | tert-butanol (g) | $X_{EL}$(%) | $S_{EP}$(%) | $X_{H2O2}$(%) | $S_{H2O2}$(%) |
|---|---|---|---|---|---|
| 12 | 0 | 20.19 | 84.27 | 95.17 | 82.72 |
| 13 | 5 | 81.74 | 96.66 | 100 | 77.07 |
| 14 | 10 | 82.64 | 92.36 | 99.62 | 74.75 |
| 15 | 20 | 82.99 | 97.23 | 100 | 81.45 |
| 16 | 30 | 82.45 | 89.82 | 100.00 | 73.89 |
| 17 | 50 | 80.50 | 87.96 | 100.00 | 70.82 |

Embodiments 18 to 20

Embodiments 18 to 20 were performed to adjust the ratio of the Ti—Si molecular sieve to ethyl lactate. Referring to the components listed in Table 7, the amount of the Ti—Si molecular sieve of Preparation 1 shown in Table 7, 20 g of tert-butanol and 5 g of ethyl lactate were provided in a 250 ml flask with a condenser tube and a stirring system. The reaction was heated to 70° C. Then, 4.11 g of hydrogen peroxide solution (35 wt %) was dropped into the reaction, and the preparation of ethyl pyruvate was performed. The introduction of hydrogen peroxide was performed for 1 hour, and then the reaction was performed for 5 hours. Upon stopping the reaction, the Ti—Si molecular sieve catalyst was separated from the reaction solution. The solution was analyzed by gas chromatography and titration. The results were shown in Table 7.

TABLE 7

| Embodiment | Ti—Si molecular sieve:EL (weight ratio) | $X_{EL}$(%) | $S_{EP}$(%) | $X_{H2O2}$(%) | $S_{H2O2}$(%) |
|---|---|---|---|---|---|
| 18 | 0.05:1 | 20.19 | 84.27 | 95.17 | 82.72 |
| 19 | 0.2:1 | 81.74 | 96.66 | 100 | 77.07 |
| 20 | 0.3:1 | 82.45 | 89.82 | 100.00 | 73.89 |

In the present invention, the Ti—Si molecular sieve catalyst is easily filtered and recycled, and hydrogen peroxide is used, such that the reaction conditions are mild, and the process is simple and easily performed. The energy consumption of the gas reaction with a gas/solid catalyst in the prior art is eliminated in the present invention. Moreover, the conversion rate of lactate ester and the selectivity of pyruvate ester are high in the present invention.

The invention has been described using exemplary preferred embodiments.

However, it is to be understood that the scope of the invention is not limited to the disclosed arrangements. The scope of the claims, therefore, should be accorded the broadest interpretation, so as to encompass all such modifications and similar arrangements.

What is claimed is:

1. A method for preparing a pyruvate ester, comprising the step of:
    performing an oxidation of a lactate ester by hydrogen peroxide in the presence of a Ti—Si molecular sieve and an aromatic hydrocarbon to obtain a pyruvate ester having a structure of formula (I):

(I)

wherein R is a linear or branched $C_{1-4}$alkyl.

2. The method of claim 1, wherein the lactate ester has a structure of formula (II):

(II)

wherein R is a linear or branched $C_{1-4}$alkyl.

3. The method of claim 1, wherein the Ti—Si molecular sieve has a structure of MFI, MEL, BEA, ZSM-48, MTW, MCM-41 or MWW.

4. The method of claim 1, wherein the weight ratio of the solvent to the lactate ester is in a range of from 10:1 to 0:1.

5. The method of claim 1, wherein the weight ratio of the Ti—Si molecular sieve to the lactate ester is in a range of from 0.05:1 to 0.3:1.

6. The method of claim 1, wherein the molar ratio of the hydrogen peroxide to the lactate ester is in a range of from 1:1 to 3:1.

7. The method of claim 6, wherein the molar ratio of the hydrogen peroxide to the lactate ester is in a range of from 1:1 to 1.25:1.

8. The method of claim 1, wherein the lactate ester is oxidized at a temperature in a range of from 50 to 80° C.

* * * * *